United States Patent [19]
Wojke

[11] Patent Number: 5,849,065
[45] Date of Patent: Dec. 15, 1998

[54] DEVICE FOR SEPARATING GAS BUBBLES FROM FLUIDS, IN PARTICULAR BLOOD

[75] Inventor: Ralf Wojke, Bad Homburg v.d.H, Germany

[73] Assignee: Fresenius AG, Bad Homburg v.d.H., Germany

[21] Appl. No.: 842,955

[22] Filed: Apr. 25, 1997

[30] Foreign Application Priority Data

Apr. 27, 1996 [DE] Germany .................. 196 17 036.2

[51] Int. Cl.⁶ .................................................. B01D 19/00
[52] U.S. Cl. ............................. 96/211; 95/254; 95/261; 96/219; 210/188; 210/304; 210/436; 604/4; 604/126; 604/406
[58] Field of Search .......................... 95/241, 254, 260, 95/261, 46; 96/6, 195, 204, 206, 208, 209, 211, 216; 210/188, 304, 436, 472; 604/4, 5, 126, 406, 405

[56] References Cited

U.S. PATENT DOCUMENTS

| | | | |
|---|---|---|---|
| 4,013,072 | 3/1977 | Jess | 210/436 |
| 4,345,919 | 8/1982 | Wilkinson et al. | 95/261 |
| 4,411,783 | 10/1983 | Dickens et al. | 210/472 |
| 4,662,906 | 5/1987 | Matkovich et al. | 96/178 |
| 4,664,682 | 5/1987 | Monzen | 96/219 |
| 4,690,762 | 9/1987 | Katsura | 210/472 |
| 4,758,337 | 7/1988 | Kohn et al. | 96/219 |
| 4,806,135 | 2/1989 | Siposs | 96/178 |
| 4,919,802 | 4/1990 | Katsura | 96/209 |
| 4,932,987 | 6/1990 | Molina | 96/219 |
| 4,964,984 | 10/1990 | Reeder et al. | 96/219 |
| 5,045,096 | 9/1991 | Quang et al. | 210/436 |
| 5,258,127 | 11/1993 | Gsell et al. | 95/260 |
| 5,312,479 | 5/1994 | Weinstein et al. | 96/209 |
| 5,484,474 | 1/1996 | Weinstein et al. | 96/209 |
| 5,632,894 | 5/1997 | White et al. | 210/472 |
| 5,651,765 | 7/1997 | Haworth et al. | 604/4 |
| 5,674,199 | 10/1997 | Brugger | 604/4 |

FOREIGN PATENT DOCUMENTS

| | | |
|---|---|---|
| 161 803 | 11/1985 | European Pat. Off. . |
| 676 213 | 10/1995 | European Pat. Off. . |
| 728 509 | 8/1996 | European Pat. Off. . |
| 35 43 126 | 6/1986 | Germany . |
| 43 29 385 | 3/1995 | Germany . |
| 2 041 233 | 9/1980 | United Kingdom . |
| 2 063 108 | 6/1981 | United Kingdom . |

*Primary Examiner*—Duane S. Smith
*Attorney, Agent, or Firm*—Kenyon & Kenyon

[57] ABSTRACT

A device for separating gas bubbles out of medical fluids, in particular blood, has a substantially cylindrical chamber, an inlet connection arranged in the longitudinal direction of the chamber, an outlet connection and a flow-guide member attached to the inlet connection and having a plurality of flow channels, which extend in a space curve out of the longitudinal direction of the chamber in a direction running substantially tangential to the inner wall of the chamber. An orifice, which is sealed by a hydrophobic membrane, is provided in the cover part of the chamber. Since the outlet orifices of the flow channels are arranged directly underneath the cover part, the membrane is circumflowed by the inflowing fluid, avoiding the formation of dead zones. The device makes it possible to separate out air bubbles with a substantial degree of reliability, without the danger of the hydrophobic membrane becoming obstructed from contact with the blood.

10 Claims, 5 Drawing Sheets

DEVICE FOR SEPARATING GAS BUBBLES FROM FLUIDS, IN PARTICULAR BLOOD

FIELD OF THE INVENTION

The invention relates to a device for separating gas bubbles out of fluids, in particular blood.

BACKGROUND INFORMATION

When blood is removed from a patient's natural blood circulatory system and is passed through an artificial extracorporeal blood circuit, any air bubbles contained in the blood must be separated out before the blood is returned to the patient. Air bubbles must be separated out of the blood, for example, in the case of blood autotransfusion and cell separation during an operation, as well as in the case of hemodialysis or hemofiltration.

The known devices for separating air bubbles out of medical fluids such as blood can also be used for separating out gases other than air. For that reason, air separators of this kind are also described as degassing devices.

Degassing blood devices must reliably separate air bubbles from the blood, and the air separator must be so constituted with respect to its mechanical properties and the flow paths being formed that any damage to the blood components is ruled out.

The air separator disclosed by GB Patent Application 2 063 108 A has a vertically arranged chamber with a cylindrical section that changes over into a conical section. Provided at the tip of the conical end fitting of the chamber is a venting bore. The fluid to be degassed enters beneath the conical section into the chamber. The inlet connection is so disposed that the fluid flows tangentially into the chamber in the outer peripheral area. Because the fluid is introduced tangentially, it initially flows in a circular flow path, but with the entire fluid motion through the chamber being superimposed upon it, so that the fluid flows through the chamber in a helical flow path and emerges again at the bottom end of the chamber out of the tangentially arranged outlet connection. In this context, the circular motional components of the fluid flow produce centrifugal forces, which build up pressure differences in the fluid, so that the air bubbles are forced to the middle of the chamber and rise upwards. The separated air bubbles can then be drawn off through the venting bore at the top end of the chamber.

German Patent Application No. 4329385 AI (published for opposition) describes an air separator comprising a flow-guide member situated downstream from the inlet connection and having two spaced apart rotation bodies, two guide blades extending therebetween. The guide blades define flow channels, which extend in a space curve out of the longitudinal direction of the chamber in a direction running substantially tangential to the inner wall of the chamber. The rising air bubbles form an air cushion in the upper part of the chamber. The fluid-outlet orifices of the flow-guide member are disposed at an ample distance from the cover part of the chamber, assuring their placement underneath the fluid level forming in the chamber.

During respiration, the times of contact between the blood components and the air are less than one second. Longer contact times trigger different control mechanisms, such as blood coagulation. However, in an extracorporeal circulation circuit, the blood-air contact can lead to complications, even to abrupt termination of the treatment. In this respect, the air volume enclosed in the known air separators in the top section of the chamber proves to be disadvantageous.

SUMMARY OF THE INVENTION

It is the underlying object of the invention to create a device for separating gas bubbles out of fluids, in particular blood, which will enable blood-air contact to be avoided and still permit air to be separated from the blood with substantial reliability, even after several hours of use.

In the device according to the invention, at least one orifice, which is sealed by a hydrophobic membrane, is provided in the cover part of the chamber, i.e., at the highest point of the chamber. The hydrophobic membrane allows gases to pass through the membrane, but does not allow the passage of fluids from the chamber. When the chamber is filled, the air enclosed in the chamber escapes across the hydrophobic membrane. Provided that the system pressure is above atmospheric pressure, the chamber can be completely filled with fluid. Pressure conditions of this kind exist, for example, when the device according to the invention is connected into the arterial blood line downstream from the blood pump or into the venous blood line. This pressure above atmosphere is produced by the blood pump arranged in the extracorporeal circulation circuit in order to induce a large enough flow in the system. For safety reasons, pressure is monitored during the extracorporeal circulation treatment, for example, the pressure may be monitored in the venous branch of the extracorporeal circulation circuit. A pressure reversal cannot occur, because if the pressure falls below a lower limiting value, an alarm is activated, and the dialysis unit is transferred to a safe operating state.

In the case of the device according to the present invention, the flow in the chamber is formed so that no dead zones occur, and the membrane in the cover part is completely circumflowed by the fluid. The section of the at least one flow channel running substantially tangential to the inner wall of the chamber is arranged directly beneath the cover part. In an arrangement of this kind, a strong fluid motion is generated along the membrane situated in the cover part. The radial and rotating flow guidance entrains any air bubbles settling underneath the cover part, enabling them to escape through the membrane. Since the air bubbles are entrained, there is no need for the membrane to extend over the entire top side of the chamber. In one embodiment of the present invention, the membrane is situated on just a portion of the surface of the cover part, which is advantageous from a cost standpoint. Furthermore, with respect to this embodiment, in the event that the chamber has not been exactly positioned, and the part of the cover surface without a membrane is situated above the part of the cover surface with a membrane, a lasting air cushion is not able to form because of the special flow guidance.

In addition, it turns out that the permeability to air of a membrane circumflowed by blood only decreases marginally over time, while a membrane that is not circumflowed by blood loses its permeability to air after extended contact with blood. Since dead zones are prevented from occurring, the device according to the invention makes it possible for gas bubbles to be separated out of medical fluids very reliably, even after several hours of use. The device according to the present invention allows the chamber to be completely filled with fluid, and has a long service life because the membrane is highly permeable to air even when accompanied by blood contact for extended periods of time. No air is enclosed in the chamber, and undesired blood-air contact does not occur.

Moreover, in known related-art chambers where air cushions are formed in the upper chamber area, fluid inflow must be placed as deeply as possible in order to stabilize the fluid layer and to avoid a renewed supply of air. This placement of the fluid inflow in related art chambers necessitates the use of a chamber having a substantial overall height. In contrast, the overall height of the chamber of the device according to the present invention can be minimized, making it possible to economize on material costs.

In one preferred specific embodiment, the flow-guide member has a central tubular connecting piece which is secured to the inlet connection. The central connecting piece is able to be fittingly inserted into the inlet connection. However, the connecting piece may likewise be a one-piece component of the inlet connection. The connecting piece of the flow-guide member changes over into at least one flow-guide tube, which extends in a space curve out of the longitudinal direction of the chamber in a direction running substantially tangential to the inner wall of the chamber. It is essential that the connecting piece be short, so that the outlet orifices of the flow-guide tubes lie closely underneath the bottom side of the cover part.

The flow-guide tubes of the flow-guide member according to the present invention allow for an uninterrupted flow guidance, with shocks being substantially avoided, so that a uniform flow profile is produced in the fluid to be degassed. This leads to low and uniform shear tangential stresses, so that the separation of air bubbles entails minimal damage to the blood.

The flow-guide member preferably has two flow-guide tubes, disposed with their orifices extending in opposite directions. This ensures that the two flows do not overlap and that vorticity is avoided in the area of the flow-guide member.

The orifice that is sealed by the hydrophobic membrane in the cover part is preferably circular in shape. However, it can also be rectangular, oval or annular. To improve air separation, the circular orifice arranged next to the central inlet connection should extend across the entire available width of the cover part, i.e., between the central inlet connection and the inner wall of the chamber. Alternatively, rather than having one orifice, the cover part may also have a plurality of orifices distributed over its periphery between the central inlet connection and the inner wall of the chamber.

In another preferred specific embodiment of the invention, the flow-guide member has a rotationally symmetric base member, whose surface facing the inflowing fluid is provided with guide blades that are curved in planes running vertically to the axis of rotation. The flow channels that are laterally delimited by the guide blades define helical flow paths. The circular motional components of flow assure that the membrane is optimally circumflowed and lead to an improved air separation.

The flow-guide member preferably has a second rotationally symmetric member, advantageously arranged at a distance, upstream from the base member, forming a plurality of enclosed flow channels at its upper side. This provides for a precise flow guidance, and makes it possible to substantially avoid flow separations, as well as the inducement of vortex flows, which is advantageous from the standpoint of minimal damage to the blood.

DETAILED DESCRIPTION

Figure 1:
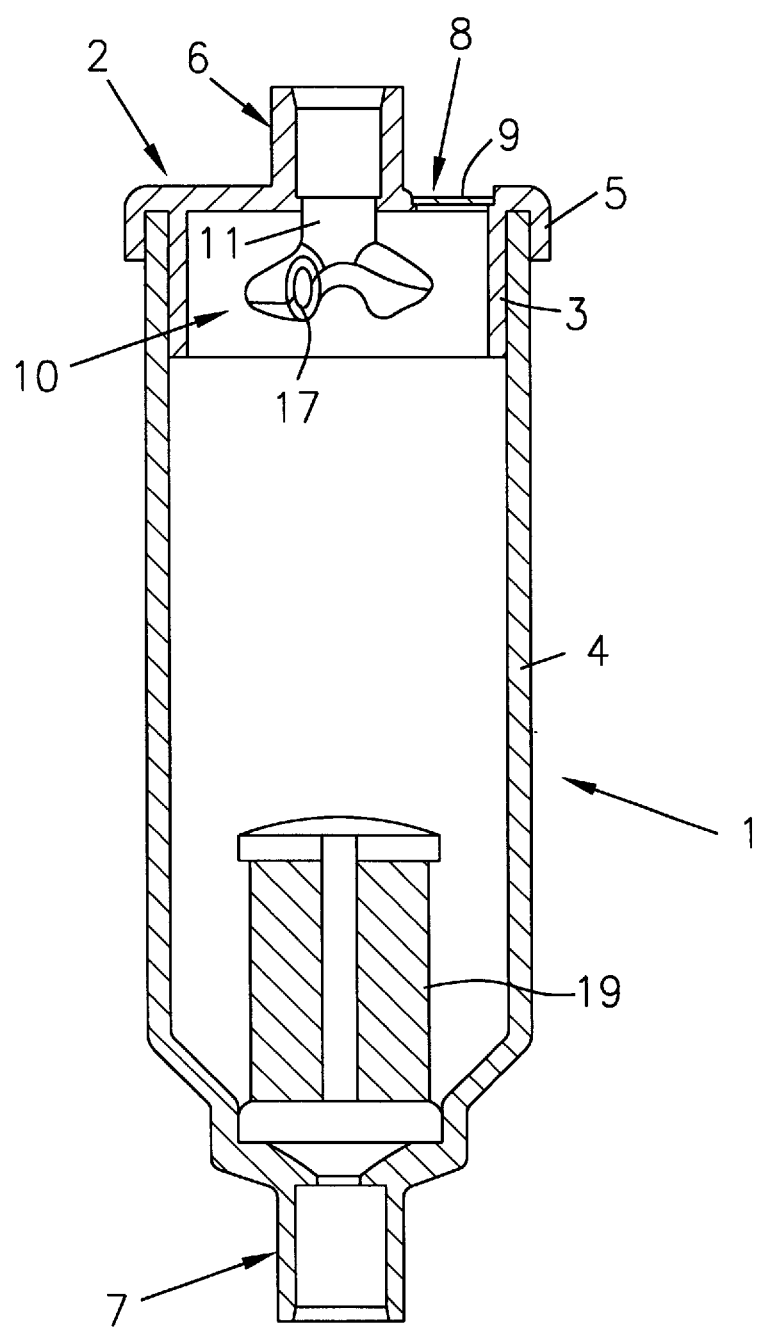
FIG. 1 shows a longitudinal section through a first specific embodiment of the air separator according to the present invention.

FIG. 1 shows a partial cut-away view of the vertically arranged air separator. The air separator has an essentially circular-cylindrical chamber 1 that is sealed at its upper end by a cover 2, which is provided with a cylindrical flange 3 and a circumferential rim 5 overlapping wall 4 of chamber 1.

Figure 2:
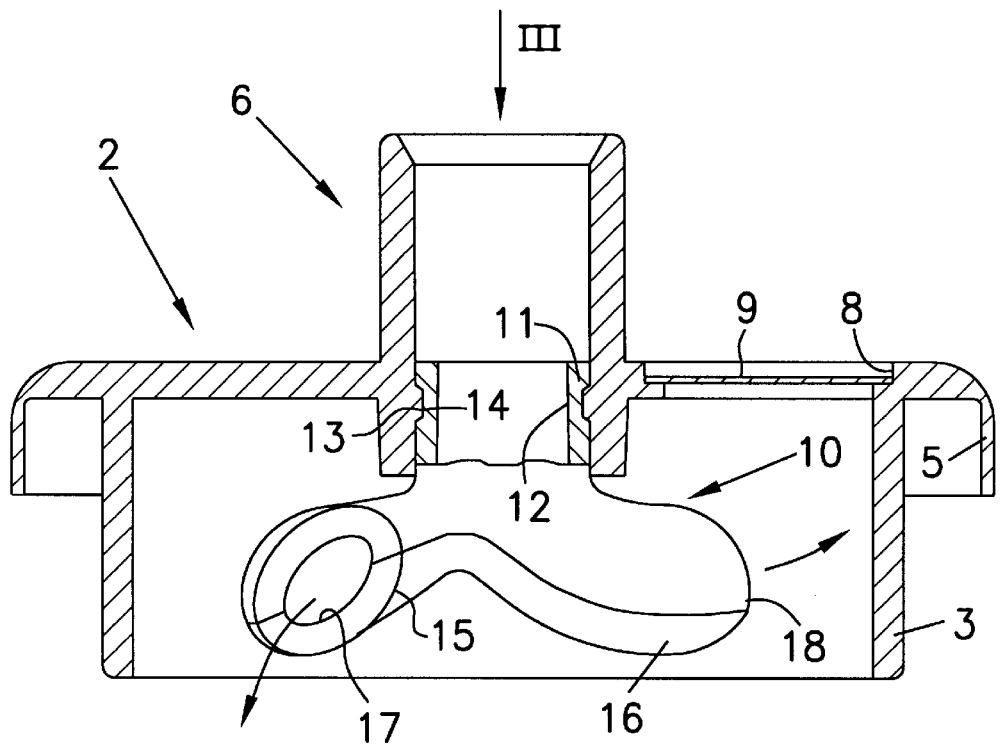
FIG. 2 shows the cover of the chamber according to the present invention with the flow-guide member in a partially cut-off enlarged representation.
Figure 3:
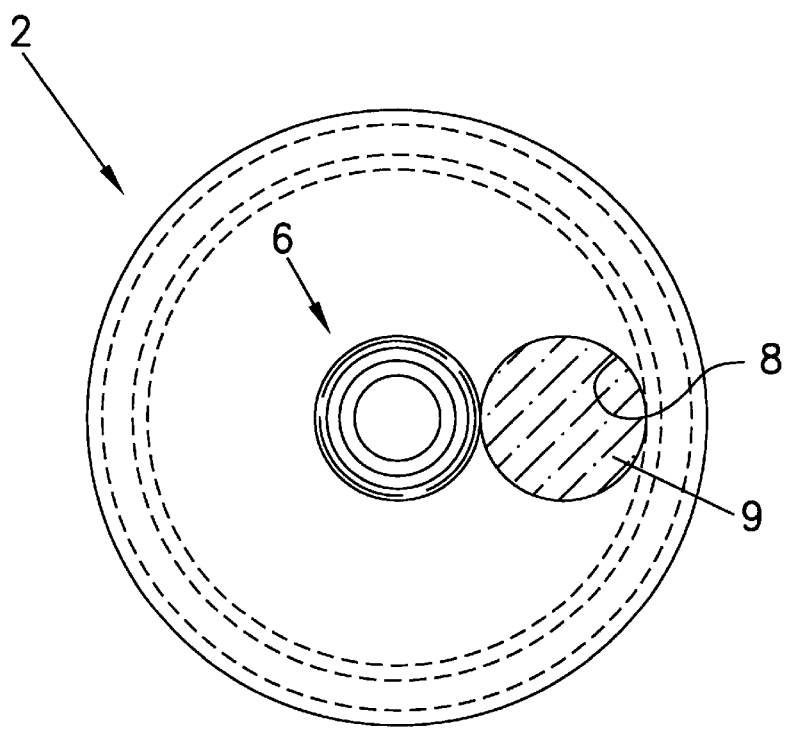
FIG. 3 shows a view of the chamber cover of FIG. 2 from the direction of the arrow III.

Arranged in the center of cover 2 is an inlet connection 6 for attaching a supply intake line (not shown), and arranged at the lower end of chamber 1 is an outlet connection 7 for attaching an outlet line (not shown). The inner diameters of inlet connection 6 and oulet connection 7 each form a press fit with the diameter of the connecting tubes to be inserted therein. Inlet connection 6 is formed in one piece with cover 2. Cover 2 includes a circular orifice 8 adjacent to inlet connection 6. Circular orifice 8 which extends from inlet connection 6 to wall 4 of chamber 1, is sealed in a fluid-tight manner by a circular, hydrophobic membrane 9 (FIGS. 2 and 3). Arranged downstream from inlet connection 6 is a flow-guide member 10, which is described in detail in the following, with reference to FIGS. 2 through 7.

Flow-guide member 10 has a short connecting piece 11, which is disposed in the longitudinal direction of chamber 1, comprises a central flow channel 12, and is inserted fittingly into inlet connection 6 of cover 2. At one inner side, inlet connection 6 is provided with a circumferential projection 13, which mates with a circumferential groove 14 on connecting piece 11 of flow-guide member 10. Connecting piece 11 changes over into two fluid-guide tubes 15 and 16 which form a one-piece component of connecting piece 11 and are symmetrically designed with respect to the longitudinal axis of the chamber. To clarify this, FIG. 2 shows central connecting piece 11 in a sectional view, while the two flow-guide tubes 15 and 16, i.e., the lower part of flow-guide member 10, are shown in a perspective view. Starting from central connecting piece 11 disposed in the longitudinal direction of the chamber, flow-guide tubes 15 and 16 extend to both sides in a space curve, in a helical shape, in a horizontal direction running substantially tangential to the inner wall of chamber 1. In this context, orifices 17 and 18 of the two flow-guide tubes 15 and 16, projecting like wings, point in opposite directions, one of the two orifices 18 being situated closely underneath orifice 8, sealed by membrane 9 in cover 2. Over their length, flow-guide tubes 15 and 16 have an substantially uniform channel cross-section that is more or less half as large as the channel cross-section of central connecting piece 11. The two orifices 17 and 18 of flow-guide tubes 15 and 16 are arranged directly underneath the bottom side of cover 2. The distance between the bottom side of cover 2 and the top edge of outlet orifices 17 and 18 corresponds more or less to the outer diameter of flow-guide tubes 15 and 16.

During operation, the chamber is completely filled with blood. Because of the special design of flow-guide member 10, the blood flowing in through inlet connection 6 into central connecting piece 11 of the flow-guide member is directed in the two flow-guide tubes 15 and 16 radially to the outside and, in this context, additionally so rerouted that, upon emergence from the flow-guide tubes, it flows in a horizontal direction, running substantially tangential to the inner wall of the chamber. Thus, the vertical flow is diverted into a horizontal circulation flow. This induces a helical flow, the circular components building up a pressure difference which leads to the air bubbles being forced in the direction of the longitudinal axis and, because of their low density, rising upwards, and escaping from chamber 1 through hydrophobic membrane 9. Since a circular flow develops directly underneath the cover of the chamber, hydrophobic membrane 9 is circumflowed with blood, and no dead zones occur where air bubbles can collect. Because of the vigorous fluid flow along the membrane, the membrane retains its permeability to air, even when used for several hours.

After the blood has flowed through the chamber 1, from top to bottom in helical paths, it flows off through a filter candle designated by reference numeral 19 in FIG. 1, and then through outlet connection 7 for further use. However, another possibility is that just inlet connection 6 is arranged in the longitudinal direction of the chamber, and that outlet connection 7 is attached to the chamber in a tangential direction.

Figure 4:
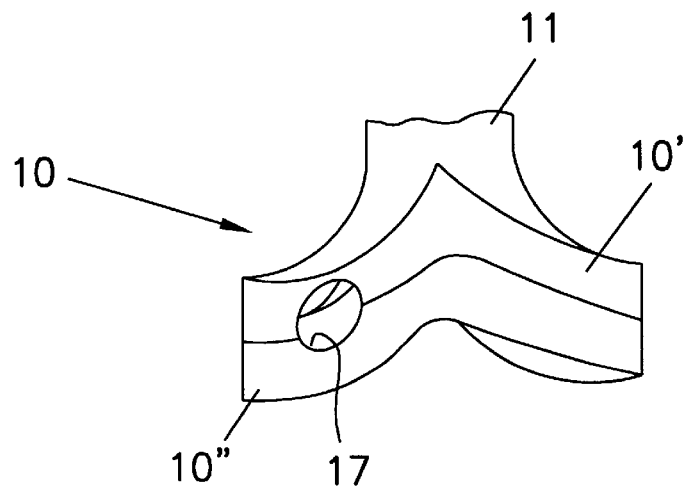
FIG. 4 shows the flow-guide member of the air separator according to the present invention comprised of two sections in an enlarged representation.
Figure 5:
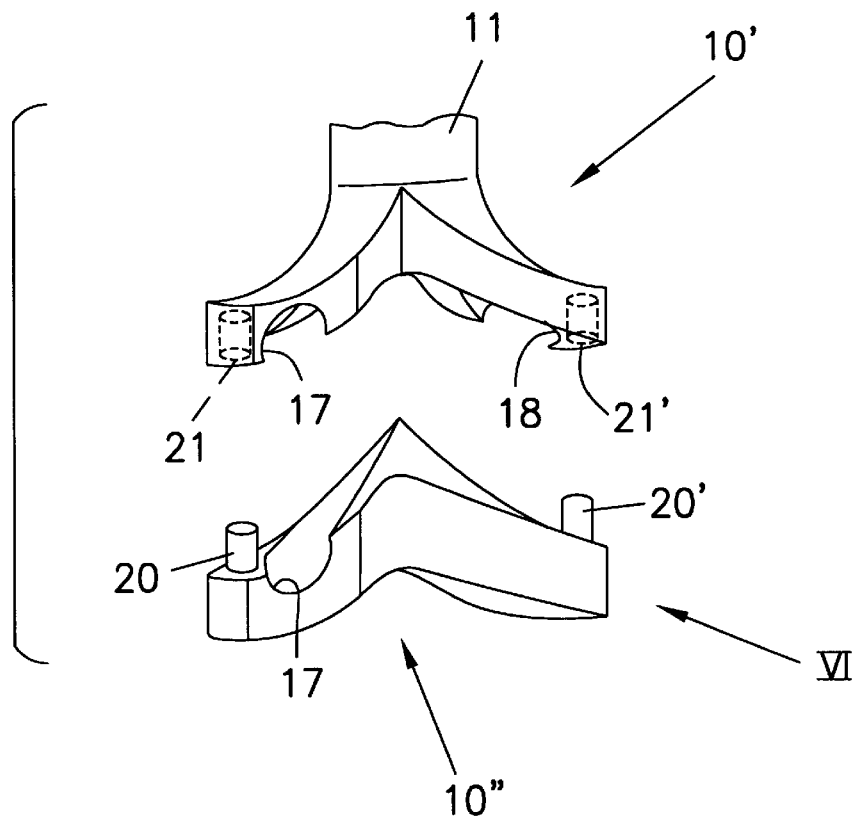
FIG. 5 shows the top and bottom section of the flow-guide member according to the present invention in a side view, prior to assembly.
Figure 6:
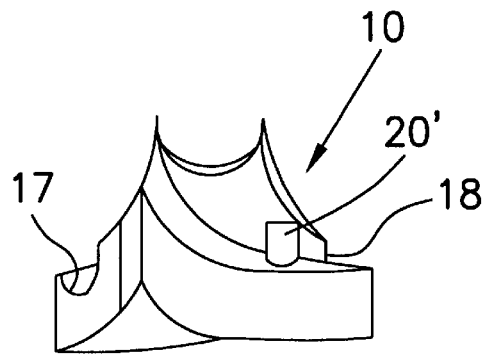
FIG. 6 shows a view of the bottom section of flow-guide member according the present invention from the direction of arrow VI as illustrated in FIG. 5.
Figure 7:
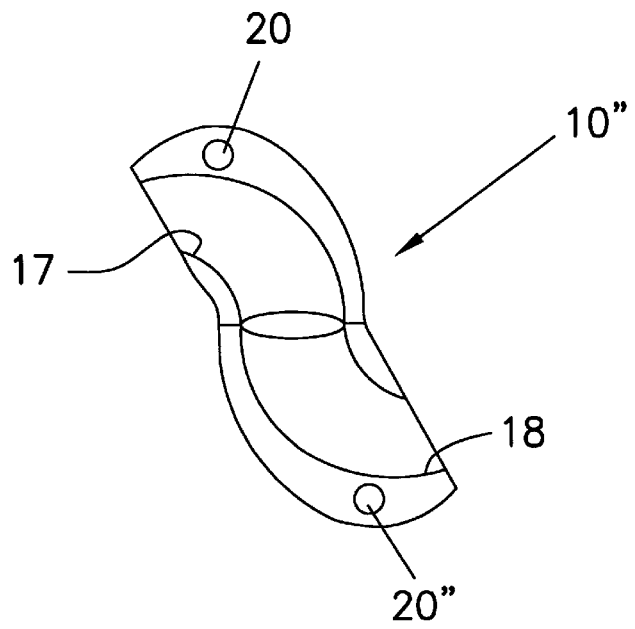
FIG. 7 shows the bottom section of the flow-guide member as illustrated in FIG. 6, in a top view.

For reasons of production engineering, flow-guide member 10 is comprised of two sections 10' and 10", which are shown in FIG. 4. Upper section 10' comprises central connecting piece 11 and the top half of the two flow-guide tubes 15 and 16, while bottom section 10" comprises the bottom half of the two flow-guide tubes 15 and 16. To enable the two sections 10' and 10" to lock into engagement and be assembled together following fabrication, provision is made on the bottom half for two pins 20 and 20', which mate in corresponding cut-outs 21 and 21' on top section 10' and hold the two parts securely together (FIG. 5).

All the air separator parts are preferably made of a transparent plastic in an injection molding operation, making it possible to optically control the filling level and the flow pattern at any time. Through the design of the flow-guide member, an air separator is created, which, because of a possible coaxial arrangement of inlet and outlet connection, is able to be simply inserted into an existing tubular system. The flow-guide member design according to the present invention allows for possible coaxial arrangement of inlet and outlet connections so that the flow guide member can be inserted into an existing tubular system, and thus, does not require a complicated manufacturing process.

Figure 8:
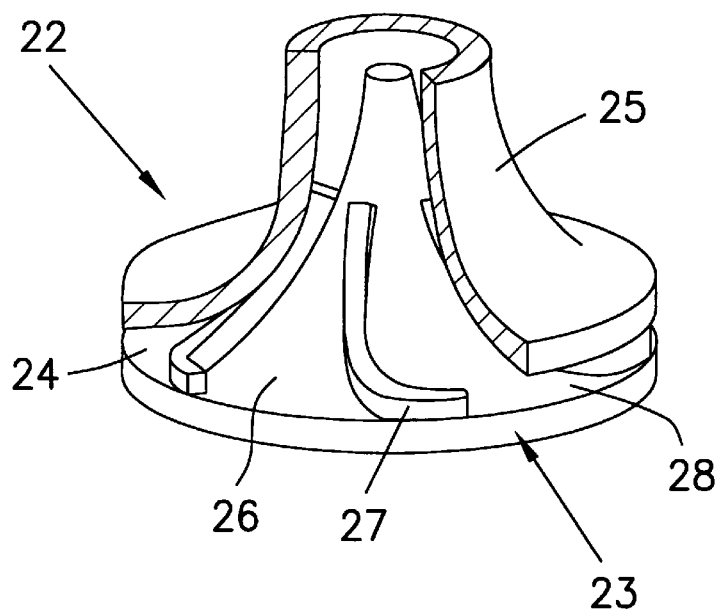
FIG. 8 shows a second specific embodiment of the flow-guide member according to the present invention secured to the inlet connection of the chamber in an enlarged, perspective view.
Figure 9:
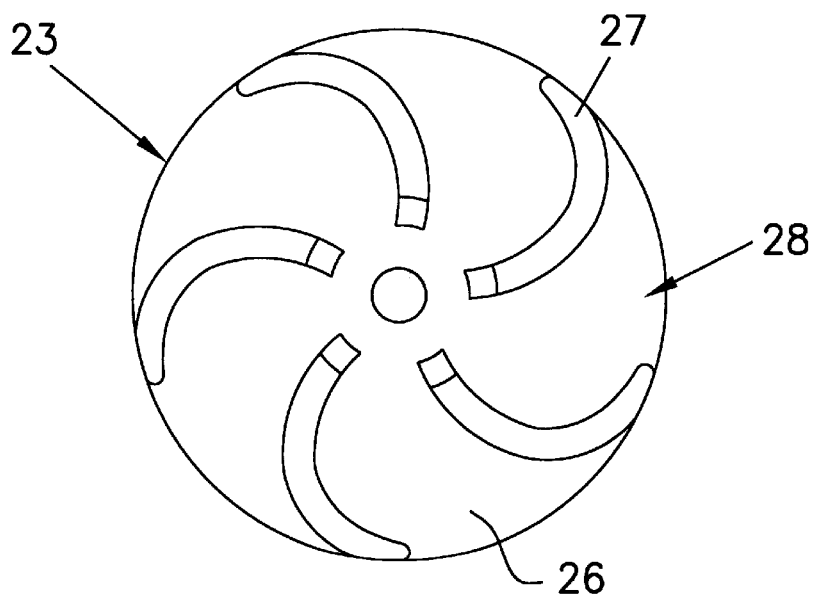
FIG. 9 shows a top view of the base member of the flow-guide member as illustrated in FIG. 8.

FIG. 8 depicts another specific embodiment of the flow-guide member, which is attached directly underneath cover 2 of chamber 1 to inlet connection 6 (not shown in FIG. 8). Flow-guide member 22 has a rotationally symmetric base member 23 whose surface facing the inflowing fluid is geometrically defined by the rotation of a concave curve section about the longitudinal axis of inlet connection 6 or of chamber 1. Arranged above base member 23 is a second rotationally symmetric member 25, which follows the concave curvature of guide baffle surface 26 of base member 23, forming a narrow gap 24. Running between the two rotation bodies 23 and 25 are a plurality of guide blades 27, which are likewise curved in planes projecting out perpendicular to the longitudinal axis of the rotation body. Guide blades 27 subdivide annular gap 24 into a plurality of flow channels 28, which extend in a space curve essentially tangential to the inner wall of the chamber 1. Since the outlet orifices of flow channels 28 are arranged directly underneath cover 2, a circular flow forms underneath the cover, so that membrane 9 is circumflowed with blood. Superimposed upon this circular flow is the flow that is directed in the longitudinal direction from inlet connection 6 to outlet connection 7. While the blood flows through the chamber, the air bubbles are separated out and removed across hydrophobic membrane 9 out of chamber 1.

What is claimed is:

1. A device for separating gas bubbles from fluids comprising:
   (a) a chamber;
   (b) a cover for sealing the chamber, having:
      (i) an inlet connection,
      (ii) at least one orifice for allowing the passage of gas bubbles from the chamber, and
      (iii) a membrane for sealing the at least one orifice; and
   (c) a flow-guide member disposed in the cover of the chamber and extending into the chamber in a direction substantially tangential to the inner wall of the chamber, the flow-guide member having at least one flow channel for delivering fluid to the chamber such that the membrane is in contact with the fluid; and
   (d) an outlet connection.

2. The device according to claim 1, wherein the flow-guide member has a tubular connecting piece secured to the inlet connection and wherein the tubular connecting piece cooperates with at least one flow-guide tube that extends into the chamber in a direction substantially tangential to the inner wall of the chamber.

3. The device according to claim 2, wherein the flow-guide member includes two flow-guide tubes having outlet orifices extending in opposite directions.

4. The device according to claim 3, wherein the first and second flow-guide tubes are symmetrical with respect to the longitudinal axis of the inlet connection.

5. The device according to claim 1, wherein the orifice of the cover is sealed by the membrane and is circular in shape.

6. The device according to claim 5, wherein the at least one orifice that is sealed by the membrane is substantially adjacent to the inlet connection of the cover.

7. The device according to claim 6, wherein the orifice that is sealed by the membrane is positioned between the inlet connection of the cover and the wall of the chamber.

8. The device according to claim 1, wherein the flow-guide member has a base member which includes at least one guide blade projecting in a direction substantially parallel to the base member.

9. The device according to claim 8, wherein the flow-guide member has a second member positioned upstream from the base member, forming an annular gap between the base member and the second member.

10. The device according to claim 9, wherein at least one of the guide blades extends to the second member of the flow-guide member.

* * * * *